United States Patent [19]

Murray

[11] Patent Number: 4,811,886

[45] Date of Patent: Mar. 14, 1989

[54] STAPLE POSITIONING TAB

[75] Inventor: Michael A. Murray, Bellevue, Ky.

[73] Assignee: Ethicon, Inc., Somerville, N.J.

[21] Appl. No.: 157,025

[22] Filed: Feb. 18, 1988

[51] Int. Cl.⁴ .............................................. A61B 17/00
[52] U.S. Cl. ................................ 227/19; 227/DIG. 1;
227/116; 227/120
[58] Field of Search .................... 227/19, DIG. 1, 121,
227/116, 120

[56] References Cited

U.S. PATENT DOCUMENTS 4,043,504  8/1977  Hueil et al. .......................... 227/116
4,196,836  4/1980  Becht ............................. 227/DIG. 1
4,410,125  10/1983 Noiles et al. .................. 227/DIG. 1
4,591,086  5/1986  Campbell et al. ..................... 227/19
4,662,555  5/1987  Thornton et al. ..................... 227/19

Primary Examiner—Paul A. Bell
Attorney, Agent, or Firm—Paul A. Coletti

[57] ABSTRACT

A flexible positioning tab is provided for placement in the staple forming track of skin staplers. This flexible tab causes only one staple from a staple stack to be moved into a staple stack for forming the staple at an anvil forming surface. This prevents the skin stapler from jamming multiple staples in the staple forming track.

7 Claims, 2 Drawing Sheets

STAPLE POSITIONING TAB

FIELD OF THE INVENTION

This invention relates generally to surgical staplers. More specifically, this invention relates to controlling staple path in surgical staplers. Most specifically, this invention relates to positioning staples within a surgical stapler during movement from a staple stack to a forming surface.

BACKGROUND OF INVENTION

In a surgical stapler, the staples generally are positioned for firing along a staple stack. This stack is capable of holding a large number of staples, and constantly urges forward the line of staples so that one staple will be in position for stapling. This one staple will generally be urged into a track where it will be guided by a driver from the staple stack to an anvil forming surface. The driver forms the staple around the anvil forming surface. After the staple is formed and released from the anvil, the driver generally will reciprocate to a non-contact position. This allows a subsequent staple to be moved into the staple forming track for stapling. When desired, the driver then urges the staple to the anvil for stapling, as before.

One of the potential drawbacks of this system is that occasionally more than one staple will become lodged in the staple forming track. When this occurs, the driver will cause the track to jam. Both staples or portions thereof are urged toward the anvil forming surface, and the initial staple and subsequent staple become wedged in the staple forming track. When this occurs, there is naturally a significant amount of delay in the use of the stapler. Also, this jamming can result in improper firing of the stapler, or breakage of the driver or other components of the stapler.

It is therefore an object of the present invention to provide a device whereby the staple track is kept clear of additional staples during the stapling procedure. That is, it is an object of the present invention to allow one and only one staple into the staple forming track at any one time. Only this arrangement insures no jamming due to an additional staple in the staple forming track.

SUMMARY OF THE INVENTION

These and other objects of the present invention are accomplished in a surgical stapler having a flexible positioning tab. This flexible tab is generally placed in the staple forming track at the head of the skin staple stack. This placement of the tab regulates the number of staples in the staple forming track. When the staple driver moves from a non-contact position to the anvil forming surface, a skin staple is urged from the staple stack. The motion of the driver and the staple causes the flexible tab to move out of the path of the driver-staple combination. During forming of the staple, the driver continues to separate the flexible tab and the staple stack. However, after forming of the staple has been accomplished, and the driver reciprocates to its original non-contact position, the flexible tab again moves into the staple forming track. This position of the flexible tab generally prevents more than one skin staple from the staple stack from entering into the staple forming track.

These and other aspects of a preferred embodiment of the present invention will be better understood from the accompanied detailed description of the drawings as well as the detailed description in which:

DETAILED DESCRIPTION OF THE DRAWINGS

DETAILED DESCRIPTION

Figure 1:
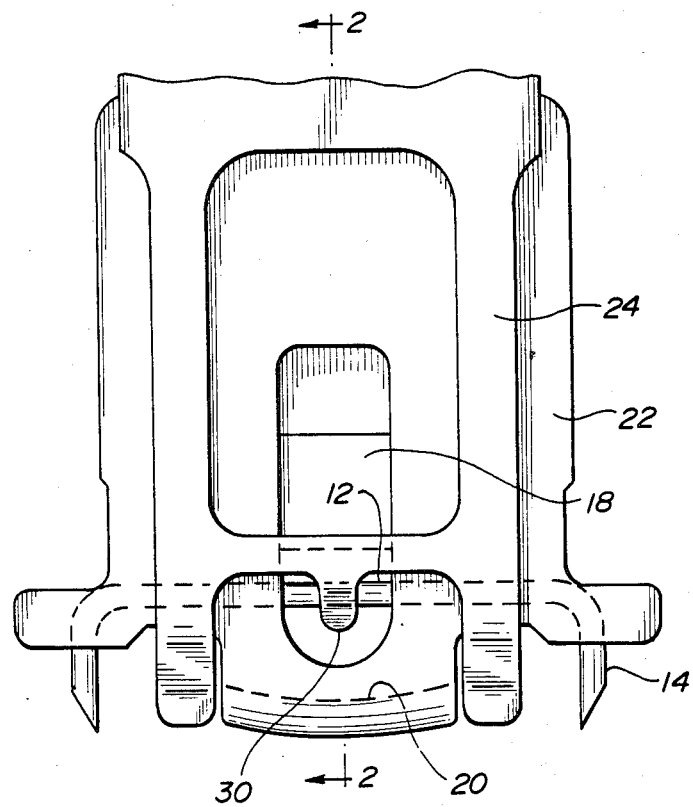
FIG. 1 is a front elevation view in cross section of a preferred embodiment of the present invention.
Figure 2:
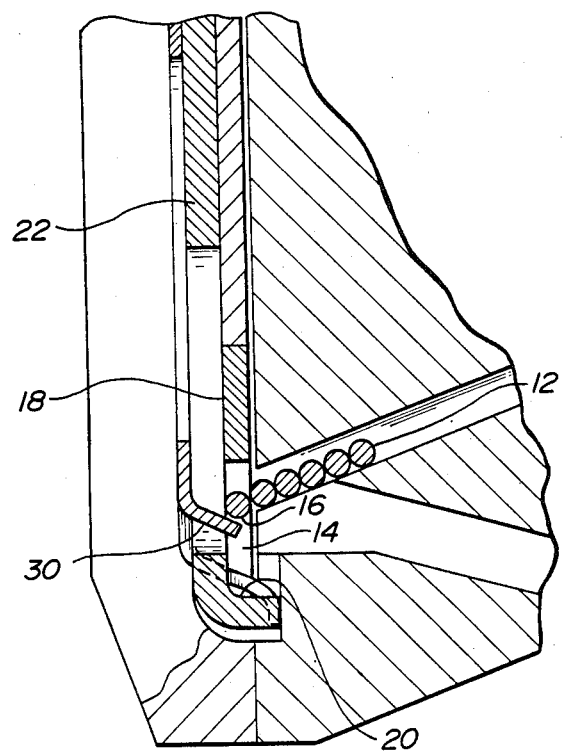
FIG. 2 is a side elevational view in cross section of a preferred embodiment of the present invention, as taken along lines 2—2 in FIG. 1.

As seen in FIGS. 1 and 2, generally in a skin stapler 10 there will be a skin staple stack 12 on which staples are urged forward by spring means not shown into a staple forming track 14. These are generally metal staples having diameters generally on the order of 0.010" to 0.023", although all types of staples can be applied to the present invention. Generally, one staple 16 is moved into the staple forming track 14. This one staple 16 will be pushed by a driver 18 against the anvil forming surface 20 of an anvil 22. When the staple 16 is moved against the anvil forming surface 20, the staple 16 will also engage a staple release spring 24. The staple 16 is caused to bend around the anvil forming surface 20 as well as deflect the staple release spring 24. Thus, the staple 16 generally takes on a box-like shape and pierces the portions of skin to be joined. After the staple 16 is formed, the staple release spring 24 causes the staple 16 to be moved off the anvil forming surface 20 and away from the stapler 10.

The flexible tab 30 of the present invention is therefore added as an additional member of the staple release spring 24. This flexible tab 30 will generally be made from a resilient material, which fits across almost the entire staple forming track 14. This flexible tab 30 sits just below the point of convergence between the skin staple stack 12 and the staple forming track 14. Thus, when the spring means in the skin staple stack 12 urges the single staple 16 into the staple forming track 14, the flexible tab 30 of the present invention is positioned to permit motion of only one staple 16 into the staple forming track 14. This is generally accomplished because the staple 16 cannot migrate toward the anvil forming surface 20 unless the staple 16 comes into contact with the driver 18.

Figure 3:
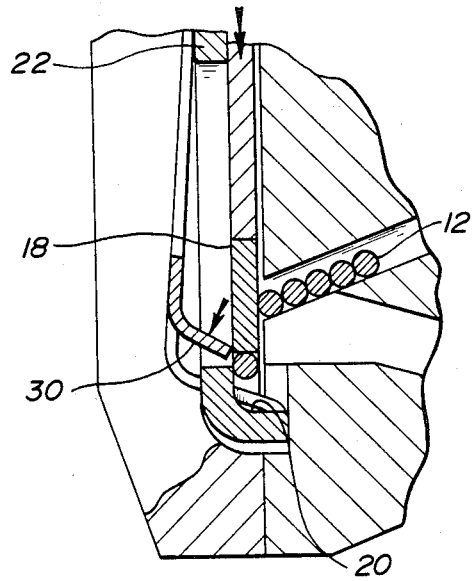
FIG. 3 is an enlarged view of the operation of the present embodiment of the flexible tab of the present invention during motion of the staple driver toward the anvil forming surface.

When the driver 18 moves from its non-contact position (as shown in FIG. 1) toward the staple 16, the flexible tab 30 goes through an elastic deflection. This deflection, as best seen in FIG. 3, causes the flexible tab 30 to move out of the path of the driver 18-staple 16 combination. The driver 18 is capable, therefore, of keeping the flexible tab 30 out of the staple forming track 14 during the entire motion of the driver 18 toward the anvil forming surface 20. Thus, during the entire forming of the staple 16 into its final box-like shape, the flexible tab 30 is separated from the skin staple stack 12. As seen in FIG. 1, when the driver moves from the anvil forming surface 20 toward its non-contact position, the flexible tab 30 of the present invention again moves into position. That is, the flexible tab 30 once again moves into the staple forming track 14. Again, the flexible tab 30 positions itself just below the point of convergence between the skin staple stack 12 and the staple forming track 14. Thus, the driver 18 will pass beyond the opening in the skin staple stack 12. With this movement of the driver 18, the spring means of the skin staple stack 12 urges a new staple 16 to move into the staple forming track 14. Because the flexible tab 30 is in position, one and only one skin staple 16 will be positioned in the staple forming track 14. Thus, accurate and efficient staple driving can take place, without any of the heretofore encountered jamming of staples within the staple forming track 14.

While this particular invention has been described in connection with the Presently preferred embodiment, it will be understood that its scope is to include any modifications to the invention which causes substantially similar functions to be performed in substantially the same way. Furthermore, it is recognized that the invention is described in connection with the attached claim.

What is claimed is:

1. In a skin stapler including a staple forming track, a driver reciprocable within said staple forming track from a non-contact position to a forming position, a staple stack constantly urging staples into said staple forming track, an anvil for forming said staples, and a staple release spring for releasing formed staples from said anvil, the improvement comprising retaining means attached to said staple release spring and positioned within said staple forming track wherein said retaining means allows the placement of only one staple from said staple stack within said staple forming track at any one time.

2. In the skin stapler of claim 1, said retaining means comprising a flexible tab pivotable out of the path of said driver when said driver reciprocates between said non-contact position and said forming position.

3. The stapler of claim 2 further comprising the flexible tab capable of extending across tee entire width of the staple forming track.

4. In a stapler having a staple forming track, said staple forming track generally providing a space for the motion of staples along said staple forming track, a staple stack comprising a plurality of staples, said staple stack having convergence with said staple forming track whereby one staple from said staple stack is generally urged into said staple forming track by spring means attached to the end of said staple stack, a driver reciprocable within said staple forming track, said driver capable of urging a staple located within said staple forming track from the point of convergence with said staple stack to an anvil located at the base end of said staple forming track, said anvil and said driver engageable with one another at an anvil forming surface such that said driver bends said staple around said anvil forming surface causing said staple to pierce the surface to be stapled at said anvil, and a staple release spring adjacent to said anvil forming surface, said staple release spring generally deflected by said staple during the engagement of said driver around said staple forming surface, said staple release spring causing said staple to move apart from said anvil upon the reciprocating of said driver during disengagement from said anvil forming surface, the improvement comprising a staple positioning tab attached to said staple release spring, the end of said staple positioning tab located within said staple forming track, said staple positioning tab preventing the entry of more than one staple from said staple stack into said staple forming track prior to the reciprocating of said driver to guide said one staple toward said anvil, said staple positioning tab deflectable from said staple forming track during the reciprocating of said driver toward said anvil.

5. In the stapler of claim 4, said staple positioning tab extending through a slot formed in said anvil such that said anvil is generally situated between said staple release spring and said staple forming track.

6. In the stapler of claim 5, said staple positioning tab extending generally across the entire staple forming track.

7. In a skin stapler, the combination comprising a staple forming track, said staple forming track generally providing a space for the motion of staples along said staple forming track, a staple stack comprising a plurality of staples, said staple stack having convergence with said staple forming track whereby one staple from said staple stack is generally urged into said staple forming track by spring means attached to the end of said staple stack, a driver reciprocable within said staple forming track, said driver capable of urging a staple located within said staple forming track from the point of convergence with said staple stack to an anvil located at the end of said staple forming track, said anvil and said driver engageable with one another at an anvil forming surface such that said driver bends said staple around said anvil forming surface, a staple release spring adjacent to said anvil forming surface, said staple release spring generally deflected by said staple during the engagement of said driver around said anvil forming surface, said staple release spring causing said staple to move apart from said anvil upon the reciprocating of said driver during disengagement from said anvil forming surface, and a staple positioning tab attached to said staple release spring, the end of said staple positioning tab located within said staple forming track, said staple positioning tab preventing the entry of more than one staple from said staple stack into said staple forming track prior to the reciprocating of said driver to guide said one staple toward said anvil, said staple positioning tab deflectable from said staple forming track during the reciprocating of said driver toward said anvil.

* * * * *